United States Patent
West

[11] 3,954,013
[45] May 4, 1976

[54] VARIABLE OPENING DEVICE

[75] Inventor: Clinton L. West, Yuba City, Calif.

[73] Assignee: Yuba City Steel Products Co., Yuba City, Calif.

[22] Filed: July 23, 1975

[21] Appl. No.: 598,209

[52] U.S. Cl. ............................. 73/423 R; 138/45
[51] Int. Cl.² ......................................... G01N 1/08
[58] Field of Search ...................... 73/421 B, 423 R; 138/45, 46

[56] References Cited
UNITED STATES PATENTS

| | | | |
|---|---|---|---|
| 2,590,215 | 3/1952 | Sausa | 138/45 |
| 3,646,971 | 3/1972 | Godet | 138/46 |
| 3,683,702 | 8/1972 | O'Brien et al. | 73/423 R |

*Primary Examiner*—S. Clement Swisher
*Attorney, Agent, or Firm*—Lothrop and West

[57] ABSTRACT

A resilient tube of predetermined length, inside diameter and outside diameter has embedded therein, in axial relation, a helical winding of substantially non-resilient material. The helix is effective to resist forces exerted on the walls of the tube by internal fluid pressure tending to change the inside and outside diameters of the tube but is ineffective to resist the forces tending to lengthen the tube as the internal fluid pressure is increased or to resist the resilience of the tube material in restoring the tube toward original length as internal fluid pressure is decreased.

By using the tube as an enclosure to define an opening, the area of the opening can be selectively varied by establishing fluid pressure within the tube at the required values; and by varying the extent of the opening as a function of sample height, an accurate core sample can be obtained when the variable opening device is used in conjunction with a sampler for bulk loads of fruits or vegetables.

12 Claims, 19 Drawing Figures

FIG_14

FIG_15

VARIABLE OPENING DEVICE

BACKGROUND OF THE INVENTION

Michael O'Brien et al U.S. Pat. No. 3,683,702 dated Aug. 15, 1972 discloses a sampler for bulk loads of fruits or vegetables. The patented sampler is especially widely used in the sampling of mechanically harvested tomatoes ultimately destined for canneries. Mechanically harvested tomatoes ultimately destined for cannery processing are ordinarily first transported to a receiving station for inspection. In recent years tomato inspection has been carried out at such stations using a sampler for bulk loads of fruits or vegetables as disclosed in said patent.

In 1971, at the time of the patent filing, about 80% of the tomatoes were received in boxes approximately 2 feet deep. Thus, the height of the core referred to in the patent was about 2 feet and the core diameter was such that as the tomatoes were released from the sampling tube, the core filled the subjacent receptacle with 50 pounds of tomatoes, the quantity required by the inspectors.

Presently, however, substantially all mechanically harvested cannery tomatoes are transported from the field to the inspection station in large bins supported on flat bed trucks or they are carried in bulk trailers. In both cases, the load is about four feet, or even more, in height. It can therefore be seen that unless something were done to constrict the central opening in the separator disclosed in the patent only the bottom two feet of the core would pass through the opening, thereby filling the receptacle before the upper two feet of core even reached the opening.

The top two feet of core would thus spill over the outside of the conical separator, rejoin the main body of tomatoes and never be sampled.

Efforts have been made to rectify the situation. For example, conical separators have been made with openings of different sizes.

By using a separator with a relatively constricted throat when a deep load is to be sampled, say four feet, or so, the core diameter is narrowed sufficiently so that the entire core length will just fill the inspection receptacle, in the manner desired.

Where a shallow load, for example, two feet, is to be sampled, a separator with the customary fairly wide throat must be used.

For loads of intermediate depth, separators with various appropriately dimensioned openings are utilized.

Owing to the fact, however, that loads are inspected in the order in which the trucks reach the receiving station rather than in accordance with the load height carried, it is frequently necessary to keep changing separators to conform to the various load heights.

This requirement becomes onerous when dozens of changes from one size separator to another become necessary during the course of a shift.

SUMMARY OF THE INVENTION

The invention relates to an attachment to a sampler for bulk loads of fruits or vegetables of the kind disclosed in U.S. Pat. No. 3,683,702 and, more particularly, to such an attachment which can be operated either in automatic mode or by hand control to vary the extent of the opening in the cone-like separator interposed between the sampling tube and the inspection sample receptacle.

The invention also relates to an extensible tube used as an enclosure defining an opening, the area of the opening being varied in dependence upon the fluid pressure established within the tube.

The invention also relates to the construction of a tube of resilient material with a non-resilient helical winding embedded therein, the helix being capable of resisting forces caused by fluid pressures tending to change the transverse dimensions of the tube but being incapable of resisting forces tending to change the axial dimensions of the tube.

It is an object of the invention to provide a variable opening device which can be utilized to especial advantage in conjunction with a separator serving to separate a desired core portion of a sample in a sampling tube from the unwanted peripheral portion of the sample surrounding the core portion.

It is another object of the invention to provide a variable opening device which can be used as an attachment to a sampler for bulk loads of fruits or vegetables of all different load heights normally encountered at a receiving and inspection station.

It is yet another object of the invention to provide a variable opening device which either by hand or automatically adjusts the core opening in a sampler separator with a minimum of effort.

It is a further object of the invention to provide a variable opening device which facilitates the inspection procedure at bulk crop receiving stations and provides more accurate inspection results.

It is yet a further object of the invention to provide a variable opening device which is relatively economical to install and maintain yet is efficient and durable.

It is another object of the invention to provide a generally improved variable opening device.

Other objects, together with the foregoing, are attained in the embodiments described in the following description and illustrated in the accompanying drawings.

SHORT DESCRIPTION OF THE DRAWINGS

FIG. 16 is a fragmentary, horizontal sectional view, to an enlarged scale, taken on the line 16 — 16 in FIG. 15;

FIG. 17 is a sectional view, to an enlarged scale of a pivot arm rotatably embracing a variable opening toroidal tube at one end and a fixed ring at the other end, the plane of the section being indicated by the line 17 — 17 in FIG. 14;

While the variable opening device of the invention is susceptible of numerous physical embodiments, depending upon the environment and requirements of use, an embodiment as shown and described herein has been made and successfully tested.

Figure 1:
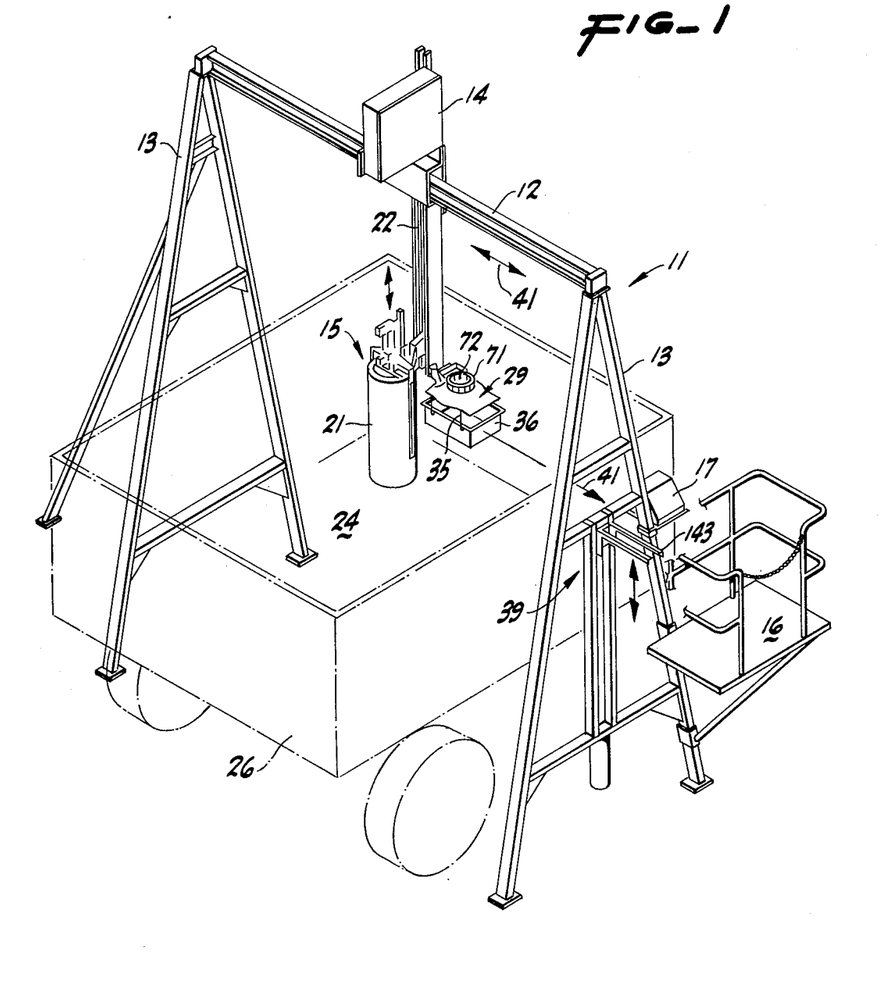
FIG. 1 is an isometric view of a bulk load sampler installation, showing in broken line a bulk container at the sampling station, a portion of the operator's platform being broken away to disclose the receptacle loading and unloading apparatus.

As appears most clearly in FIG. 1, a typical sampling installation includes a frame, generally designated by the reference numeral 11, having a transverse rail 12 supported on a pair of A-shaped end frameworks 13. A trolley 14 runs on the rail 12 carrying the sampling apparatus 15 to and fro across the transverse width of a load 24, such as tomatoes, in a bulk container 26. A platform 16 enables the operator to view the operation and a console 17 located next to the platform 16 allows the operator to control all phases of the sampling procedure.

Figure 2:
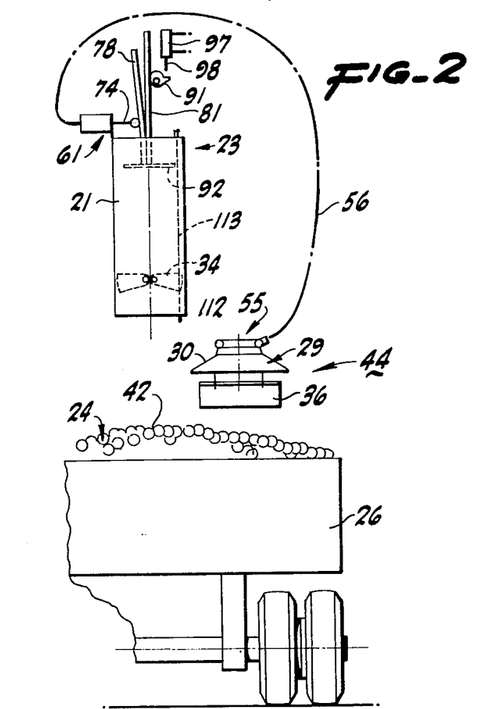
FIG. 2 is a fragmentary, schematic, rear elevational view showing a mobile bulk container with a load of fruits or vegetables, such as tomatoes, preparatory to being sampled by a sampling tube in upper position poised above the load and with the variable opening separator and receptacle temporarily disposed to one side, out of the path of the sampling tube.

The sampler 15 includes a vertical sampling tube 21 translatably mounted on a hoist 22, for movement between an upper position 23 (see FIGS. 2, 4 and 5) above the load 24 and a lower position 27 (see FIG. 3), in which the sampling tube 21 has penetrated the load 24 to a location adjacent the bottom 28 of the container 26.

After the sampling tube 21 is elevated, a separator 29 is swung into position below the tube 21 and the sample is released, as in FIG. 4. The separator 29 is a truncated cone-like member with a central opening 31 through which passes the central core 32 of a columnar sample 33 of tomatoes confined by jaws 34 within the sampling tube 21 during lifting. The sample 33 is released as the jaws 34 are opened. As the tomatoes in the sample 33 descend on the separator 29, the sloping sides 30 of the separator intercept and laterally deflect all of the tomatoes except those contained in the central core 32 which pass through the opening 31 and are deposited in a subjacent inspection receptacle 36.

Figure 14:
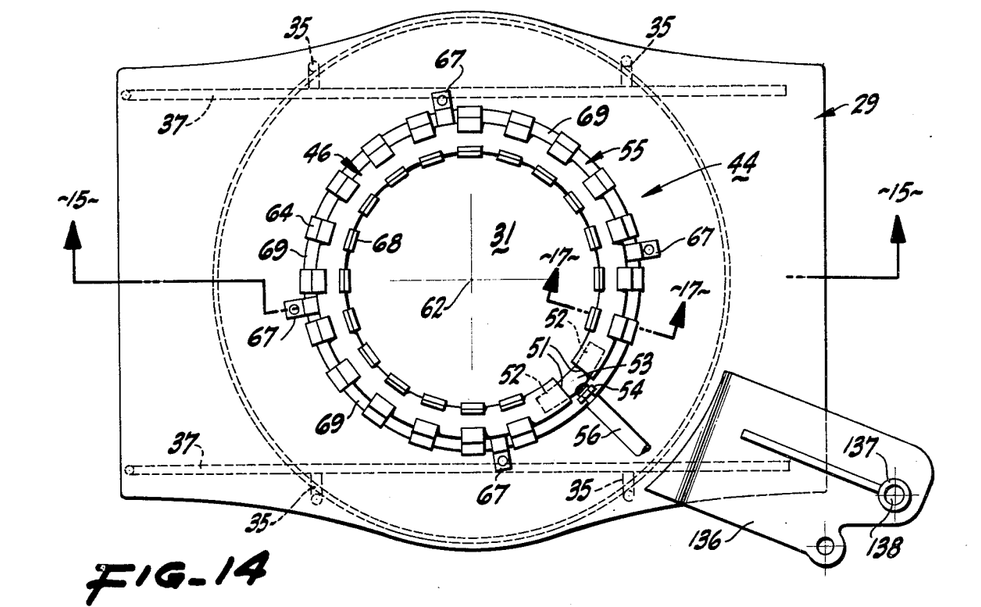
FIG. 14 is a top plan view, to an enlarged scale, of the variable opening separator and supporting arm.
Figure 15:
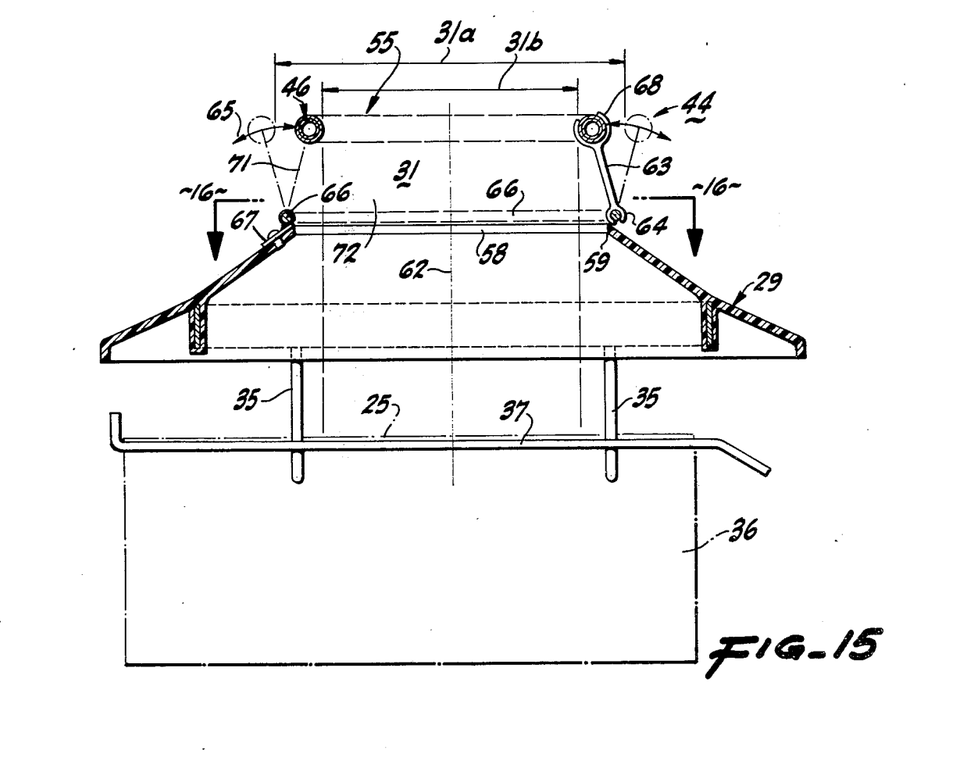
FIG. 15 is a sectional view, taken on the line 15 — 15 in FIG. 4, showing in broken line the depending, removable receptacle.

The receptacle includes a pair of laterally out-turned upper side margins 25 slidably supported on a pair of parallel rails 37 suspended on J-bars 35 depending from the separator 29 (see FIGS. 14 and 15). This construction enables a receptacle to be readily manipulated. Thus, when the trolley 14 transports the sampler and filled receptacle to the operator's platform 16 for unloading, the operator is quickly able to replace the filled receptacle with an empty one and return the trolley into position for the next sample.

Approximately fifty pounds of tomatoes are required by the inspectors for each sample and the receptacle 36 is dimensioned to receive this amount. In order properly to test a load, however, it is necessary that the sample 38 located in the receptacle 36 being carried to the unloading station 39 (see FIGS. 1 and 5) in the direction of the arrow 41 be representative of the load from top 42 to bottom 28.

Heretofore, it has been necessary to change conical separators 29 so that the appropriate area of central opening 31 in the separator could be used, depending upon the load depth as estimated by the operator. This procedure necessitated having to keep on hand, adjacent the loading/unloading station 39, a supply of separators with different sized openings. Problems of storage, identification and the task of changing from one size to another made this procedure less than satisfactory.

With the system now to be described, however, the need to replace separators for each load of different height is eliminated. Instead, the effective amount of the central opening 31 in the separator 29 is itself varied, either automatically or by hand control.

As appears most clearly in FIGS. 14 – 19, the variable opening device of the invention, generally designated by the reference numeral 44, includes a resilient tube 46 of a suitable elastomeric material having a predetermined length L, outside diameter OD and inside diameter ID.

Figures 16, 17, 19:
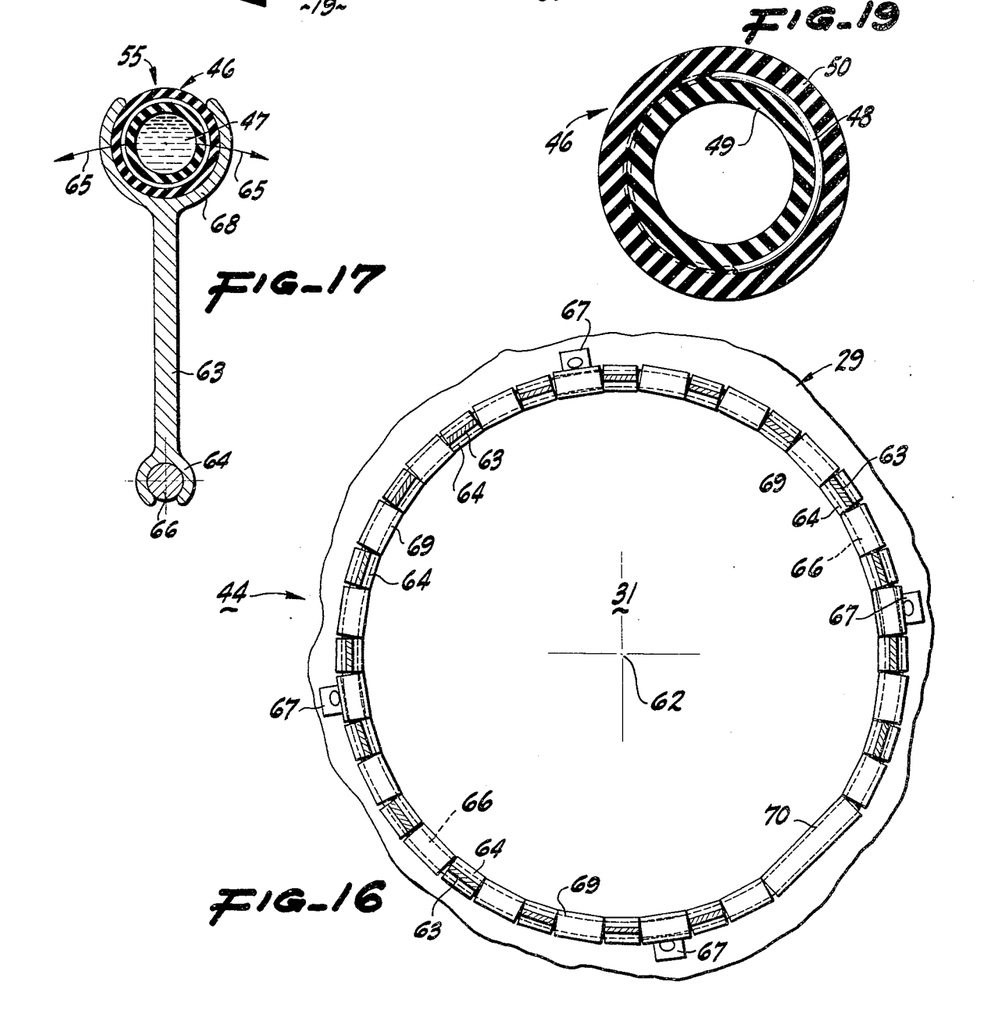
Figure 18:
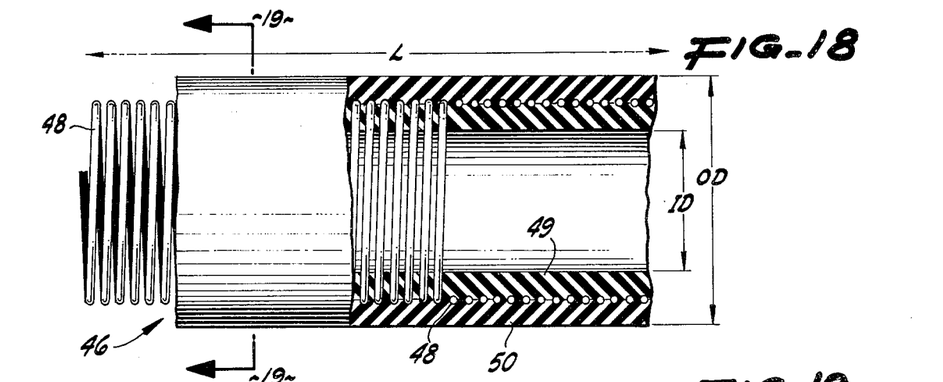
FIG. 18 is a fragmentary view, to a greatly enlarged scale, of a portion of the longitudinally extensible, but radially non-expandable tube of the invention, portions of the tube walls being broken away to reveal the non-resilient helical winding embedded in the tube; and, FIG. 19 is a transverse sectional view, to a greatly enlarged scale, of the tube, the plane of the section being indicated by the line 19 — 19 in FIG. 18.

Preferably, the tube 46 is fabricated of neoprene, for resistance to weathering, and has a hardness of about 40 to 60 Shore A.

In order to prevent changes in outside diameter OD and inside diameter ID as the pressure of a fluid 47 inside the tube is varied, yet permit changes in length L as fluid pressure variations occur, a helical winding 48, preferably of fibreglass material, is embedded in the tube.

The inner layer 49 of tube 46 is formed by applying neoprene on a straight rod, or mandrel (not shown) and is partially cured to provide sufficient strength to hold the fibreglass winding 48. The helix 48 is closely wound in a single pass. The outer cover 50 of neoprene is thereupon added and the whole is oven cured. Following withdrawal from the mandrel, the hose can be cut to length as required.

Although the variable opening device can be formed in any suitable configuration, such as a triangle, square or other polyhedron it assumes, in its preferred embodiment, a circular shape.

Thus, by recurving the two ends 51 of the tube 46 into close juxtaposition (see FIG. 14) a toroidal configuration 55 is established.

The two ends 51 of the tube 46 are closed off from the atmosphere and are held in position by the cross-limbs 52 of a T-fitting 53, the vertical limb 54 of which is connected to a fluid pressure hose 56 leading to a pressure source 61 which will subsequently be described in detail and is shown schematically in FIGS. 2 – 5.

Since the fibreglass helix 48 prevents changes in the OD and ID but allows the length L to vary in dependence upon the internal fluid pressure in the tube 46, it follows that the diameter 57 (see FIG. 11) of the toroid 55 increases and decreases as a direct function of the pressure applied to the fluid within the tube by the pressure establishing means 61.

By installing such a toroid 55 above the fixed circular opening 58 in the separator 29, as appears most clearly in FIG. 15, the effective area of the opening 31 can be selectively varied to conform to respective load heights, thereby eliminating the necessity of having to change separators each time a load of different height is encountered.

Where the load height is minimal (2 feet, for example) the internal fluid within the tube 46 can be increased so as to cause the toroid 55 to expand to maximum diameter 31a, an amount which is substantially equal to or slightly in excess of the diameter of the fixed opening 58 in the separator 29 (see FIG. 15).

In this situation, the effective diameter of the central sample core 32 is established at the required amount for the height of the sample core 32. Thus, the tomatoes from the core 32 which pass downwardly through the opening 31a will not only fill the receptacle 36 to the required weight but will also be representative of the relatively shallow load from top to bottom.

On the other hand, where the load 24 is a very deep one (4 or sometimes more feet, as shown in FIGS. 2 – 5, for example) it is necessary to reduce the diameter of the central core 32 so that the sample portion which reaches the receptacle 36 will contain tomatoes from top to bottom of the load.

In other words, where the load is deep, and the core is long, the core diameter must be reduced to an appropriate dimension. This means that the toroid diameter must be correspondingly diminished, to the diameter 31b, for example, as shown in FIG. 15.

For convenience, the toroid and attendant fittings are customarily dimensioned so that when the toroid has been constricted to a minimum diameter 31b under its own natural resilience, the opening provided by diameter 31b will service the deepest load which might reasonably be expected. Under these conditions, the internal fluid pressure in the tube 46 will be at minimum, or base, pressure.

Then, as shallower loads are received, the fluid pressure is increased by an amount sufficient to expand the toroid by an appropriate amount. The shallower the load, the wider the toroid is enlarged in order to meter the sample to the amount required to fill the receptacle while, at the same time, acquiring specimens from all load horizons.

Figure 4:
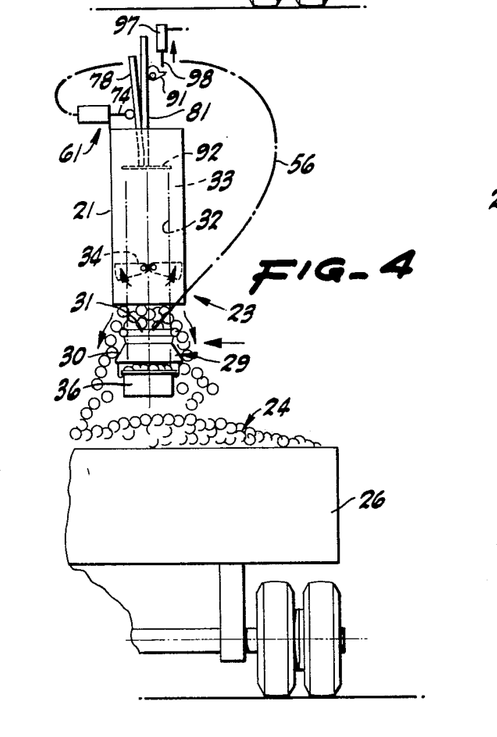
FIG. 4 is a view comparable to FIG. 2 but with the sampling tube in elevated position, with the separator located in coaxial position below the sampling tube, and with the jaws open to allow the confined columnar sample to descend onto the separator and fill the receptacle with the desired core portion passed by the variable opening device of the invention.

It has been found that by locating the toroid 55 in a horizontal plane above the horizontal plane of the circular margin 59 defining the upper fixed opening 58 in the truncated cone-like separator 29, a nice measure of control is attained with respect to the wanted core portion 32 which passes into the receptacle and the unwanted portion which falls down outside the toroid and is laterally deflected by the upper surface of the conical separator to return to the main load 24 (see FIG. 4).

Thus, as is most clearly shown in FIGS. 14 – 16, the toroid 55 is coaxially disposed on the axis 62 of the separator opening 58 and is elevated somewhat above the opening 58. The toroid 55 is sturdily supported in proper spatial relation above the opening 58 while retaining its ability to expand and contract owing to the provision of a plurality of upstanding pivot arms 63.

The pivot arms 63 are bifurcated at their lower end and are acurately shaped to provide a pair of lower fingers 64 loosely embracing a circular steel ring 66, of fixed diameter, the ring 66 being mounted coaxially on the upper surface of the rim 59 of the opening 58 by suitable fastenings 67, such as straps and riveds.

In somewhat comparable manner, similar pairs of arcuate upper fingers 68 on the upper ends of the pivot arms 63 loosely embrace the toroid 55. This construction enables the pivot arms 63 to rock back and forth, in response to changes in toroid diameter, following the arc indicated by the arrows 65 in FIGS. 15 and 17.

Separating the lower ends 64 of the pivot arms 63 is a plurality of collar-like spacers 69 disposed around the periphery of the fixed diameter steel ring 66 (see FIG. 16) in alternating fashion. An elongated spacer 70 is used along ring 66 corresponding to the space on the toroid occupied by the T-fitting 53. The pivot arms 63 form, in conjunction with the toroid, a crown or neck-shaped structure 71, upstanding from the conical separator 19, as appears in FIG. 1, the throat 72 of which varies in cross-sectional area as the toroid is expanded or contracted.

As previously indicated, the toroid diameter varies in accordance with the pressure of the fluid filling the tube 46, the fluid pressure within the tube being established, in turn by the pressure source 61 which is in communication with the tube 46 via the fluid hose 56.

Figures 9, 10:
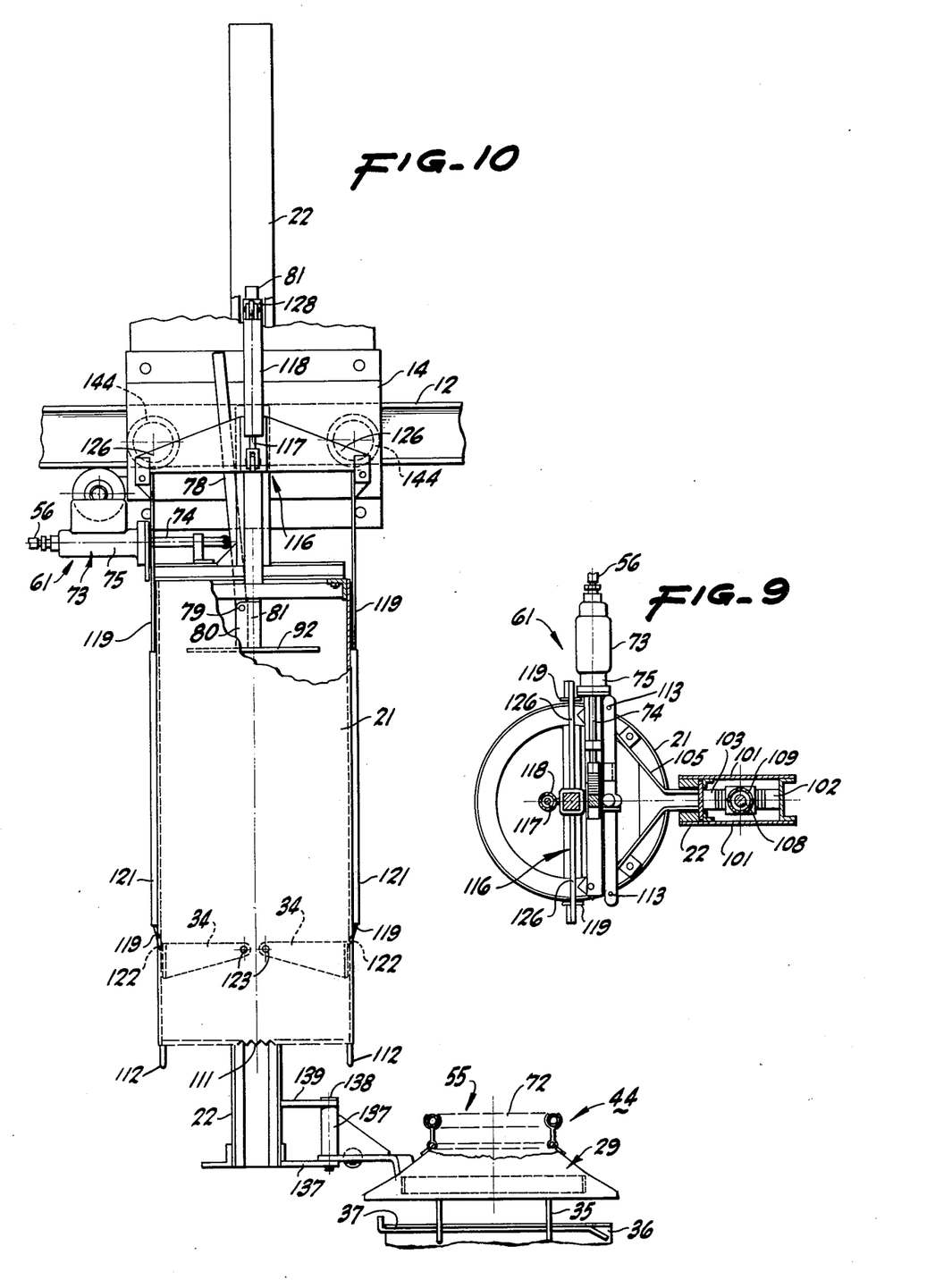
FIG. 9 is a sectional view, the compound planes of the section being indicated by the lines 9 — 9 in FIG. 6.
FIG. 10 is a fragmentary front elevational view, to an enlarged scale, of the vertical sampling tube, hoist and variable opening separator, a portion of the sampling tube being broken away to reveal details of the load depth gauge.
Figures 11, 12:
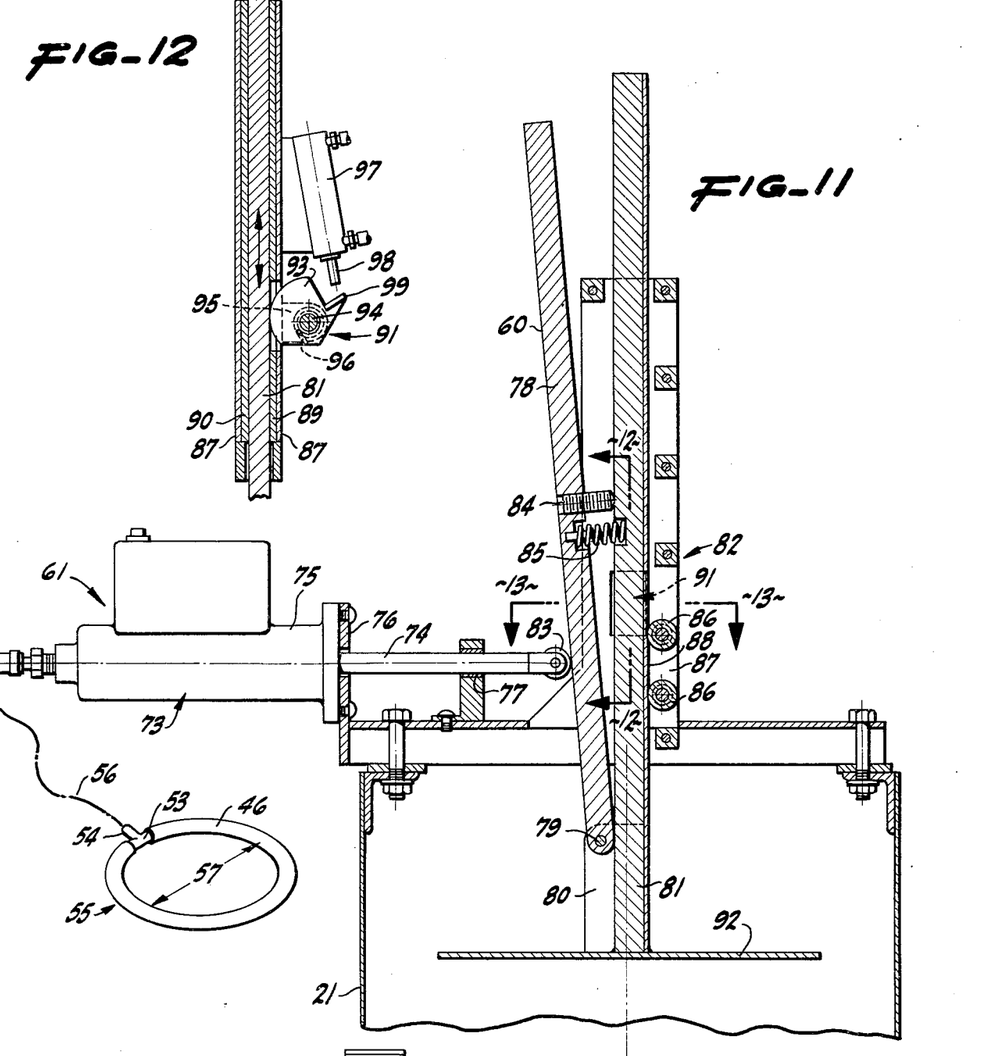
FIG. 11 is a fragmentary sectional view, to an enlarged scale, taken on the line 11 — 11 in FIG. 6, with a schematic hose connection to a variable opening toroidal form of device, the toroid being shown to a reduced scale.
FIG. 12 is a fragmentary, median, vertical, sectional view, to an enlarged scale, of the depth gauge brake mechanism; the plane of the section being indicated by line 12 — 12 in FIG. 11.

The pressure 61 comprises a conventional fluid displacement device 73 including a horizontal plunger 74 and cylinder 75 (see FIGS. 9 – 11). The fluid displacement cylinder 75 within which the plunger 74 operates is mounted on a plate 76 secured to the upper end of the vertical sampling tube 21, and the plunger 74 translates to and fro in a bearing 77 also mounted on top of the sampling tube 21.

The extent of movement of the plunger 74 is determined by the amount of displacement of a sloping linear bar cam 78 adjustably mounted on a pin 79 spanning a pair of flanges 80 secured to the vertical stem 81 of a vertically movable depth gauge, generally designated by the reference numeral 82.

The sloping cam 78 engages a roller 83 on the plunger 74. In base position, as appears in FIG. 11, for example, the plunger 74 is projected to its maximum from the cylinder 75 by an internal spring in the fluid displacement device 61. Accordingly, the fluid pressure within the fluid system is at a mimimum and the toroid is at minimum diameter. This then, would correspond to the minimum opening 31b which would be used for a sample from a load having maximum height, as in FIGS. 2 – 5 and which would also be the height in FIG. 11 of the horizontal probe plate 92 mounted on the lower end of the vertical stem 81.

Should the load depth be shallower than the maximum probe plate height in FIG. 11, the depth gauge 82 descends from the position shown in FIG. 11. As the depth gauge drops, the inclined surface 60 of the cam 78 in engagement with the plunger roller 83 biases the plunger 74 into the cylinder 75 and displaces fluid from the cylinder 75 into the hose 56 and thence into the toroid 55, thereby expanding the toroid by an amount which is dependent upon how far the depth probe 82 descends before the probe plate 92 engages the top of the load and stops. The shallower the load, the farther the depth gauge falls and the greater the amount of fluid pumped into the toroid so as to expand the opening.

Adjustment of the cam 78 is provided by a threaded spacer pin 84 and spring 85 (see FIG. 110); and vertical alignment of the stem 81 of the depth gauge 82 is secured by providing appropriate rollers 86 journaled in side plates 87 upstanding from the upper end of the sampling tube 21. The anti-friction rollers 86 engage a wear strap 88 of durable material mounted on the adjacent side of the depth gauge stem 81 and serve in conjunction with lubricated side walls 89 and 90 to keep the depth gauge stem in smoothly operating vertical attitude as the gauge translates upwardly and downwardly in the course of probing and transmits information on load depth to the pressure source 61.

Downward movement of the depth gauge stem 81 relative to the sampling tube 21 is arrested by a brake 91 at the lowest point in its descent, when the probe plate 92 carried on the lower end of the stem 81 engages the top 42 of a load as the sampling tube 21 penetrates to the bottom 28 of the load.

Figure 13:
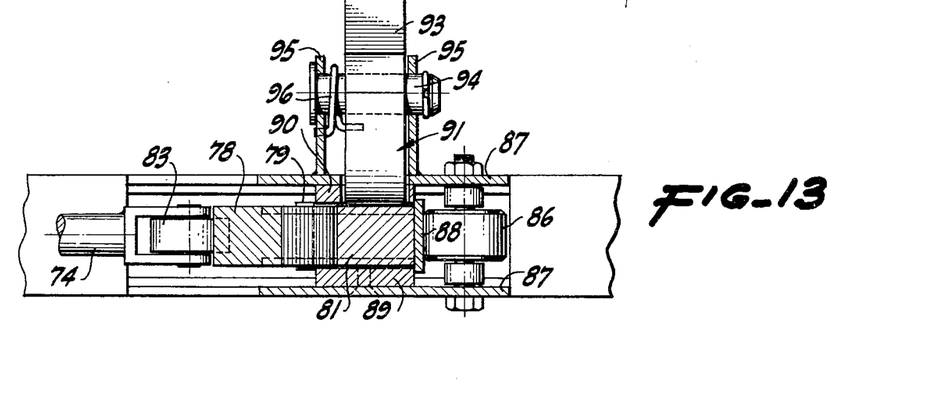
FIG. 13 is a fragmentary, horizontal sectional view, to an enlarged scale of the depth gauge brake mechanism and cam drive structure, the plane of the section being indicated by the line 13 — 13 in FIG. 11.

The brake 91 includes an eccentric cam 93 rotatably mounted on a pin 94 spanning ears 95 outstanding from one of the side plates 87. A spring 96 biases the eccentric 93 inwardly through an opening in the side walls into engagement with the depth gauge stem 81 in a direction such that the downward urgency of the weight of the depth gauge 82 tends to jam the eccentric 93 and prevent further downward movement of the depth gauge (see FIGS. 12 and 13).

In order to reverse the jamming of the eccentric 93 and release the brake 91, a jack 97 is mounted above the eccentric so that as fluid pressure is applied through the upper fitting of the jack, a ram 98 strikes a flange 99 projecting outwardly from the eccentric 93 in the path of the ram 98. Reversal of fluid pressure in the jack fittings retracts the ram 98 and again allows the spring 96 and gravity to actuate the brake.

It is to be noted that when the stem is urged upwardly, against the force of gravity, the brake is automatically released since the stem 81 engages and urges the eccentric 93 in a dejamming direction in opposition to the bias afforded by the spring 96.

Vertical movement of the sampling tube 21, as previously indicated, is provided by the hoist 22.

As appears most clearly in FIGS. 6 – 10, the hoist 22 includes a pair of vertical side plates 101, a fixed gear rack 102 and a movable gear rack 103 vertically slidable in a pair of tracks 104 (see FIG. 8)). The sampling tube 21 is mounted on the movable gear rack 103 by a horizontal yoke arm 105. A pinion 106 journaled in a clevis 107 is carried on the lower end of a piston 108 and a fluid actuated cylinder 109. The combination of movable gear rack 103, fixed gear rack 102 and interposed pinion 106 on piston 108 serves, in well known manner, to multiply the effective stroke of the piston. Thus, a vertical piston movement of 2 feet, for example, could cause the movable gear rack 103, and the sampling tube 21 connected thereto, to translate 4 feet, or even more, depending upon the dimensions.

This hoisting arrangement, in other words, multiplies the speed with which the sampling tube 21 can descent into the load to be sampled and the speed with which it can retract upwardly to base position.

As the sampling tube 21 descends, the serrations 111 around the lower end of the tube (see FIGS. 6 and 10) assist in cutting an undisturbed sample. As the lower end of the tube approaches the container floor 28 at the bottom of the load, a probe 112 comes into engagement with the floor, causing the probe rod 113 to translate upwardly against the downward bias of spring 114 (see FIG. 6) and trip a limit switch (not shown) which simultaneously halts the further downward advance of the hoist and actuates the jaw mechanism 116 so as to close the jaws 34 and thereby confine the lower end of the sample 33 inside the sampling tube 21.

The jaws 34 are opened and closed by operation of a plunger 117 and hydraulic cylinder 118 combination acting through a pair of vertical operating straps 119 on opposite sides of the tube 21, the straps each being vertically guided by a pair of tracks 121 mounted on the tube sides. The lower ends of the straps protrude inwardly through respective openings 122 in the tube side walls and are attached to the outer portions of the jaws 34 which are centrally pivoted on pins 123. The upper ends of the straps 119 are mounted on the ends of a pair of lateral arms 126 carried on a square-in-section sleeve 127 slidably disposed on a vertical, square-in-section bar 128 mounted on and upstanding from the upper end of the sampling tube 21. The upper end of the hydraulic cylinder 118 is pivotally mounted on a flange 129 extending laterally from the top of the bar 128.

Figures 6, 7, 8:
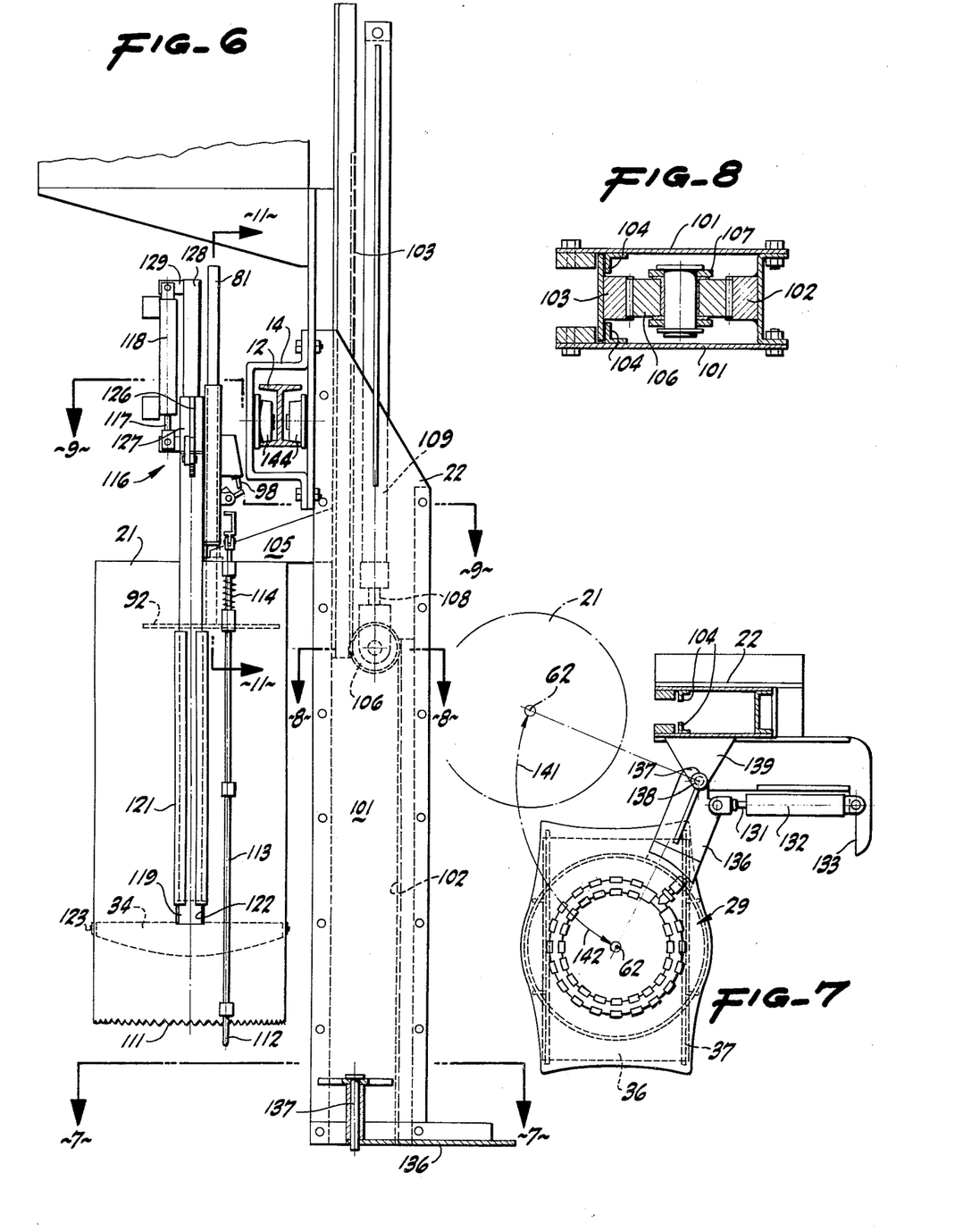
FIG. 6 is a fragmentary side elevational view, to an enlarged scale, of the vertical sampling tube, hoist and load depth gauge mechanism.
FIG. 7 is a horizontal sectional view, taken on the line 7—7, in FIG. 6 showing the construction of the separator and the path of the separator in moving between extreme locations under urgency of a ram type actuator.
FIG. 8 is a horizontal sectional view, to a greatly enlarged scale, the plane of the section being indicated by the line 8 — 8 in FIG. 6.

In order to swing the separator 29 and the sample box 36 between the base position shown in FIGS. 1 – 3, 7 and 10 and the sample receiving position in axial alignment with the sampling tube 21, as appears in FIG. 4 and in broken line in FIG. 7, a plunger 131 and cylinder 132 are provided. The cylinder 132 is pivotally mounted at its base end on an arm 133 attached to the hoist 22 structure and the plunger 131 is pivotally attached by a clevis (see FIG. 7) to a lever arm 136 attached to a sleeve 137 pivotally mounted on a vertical pin 138 supported by a spaced pair of horizontal ears 139 carried on the hoist column 22. With the plunger 131 retracted as shown in full line in FIG. 7, the separator 29 is removed from the sampling tube axis; but with the plunger 131 extended, the separator 29 is coaxially aligned with the sampling tube.

OPERATION

Although manual operation can be used, either for parts or for the whole of the cycle, automatic cycling is preferred owing to its greater speed and accuracy.

At the start of the cycle, the separator 29 and the sample box 36 are transversely oriented, as in FIG. 1, and the sampling tube 21 is elevated to its uppermost, or base, position well above the level of the separator.

The loaded container is then placed in a position as appears in FIG. 1, with the trolley 14 and depending sampling equipment located approximately in a central fore and aft plane.

The operator on platform 16 starts the cycle by appropriate manipulation of the controls on the adjacent console 17. The first step is marked by the descent of the sampling tube 21 into the load 24, the descent being halted as the lower end 112 of the probe rod abuts the container floor 28 and trips a limit switch not only temporarily stops the hoist but closes the jaws 34 to confine the sample, as shown in FIG. 3.

Figure 3:
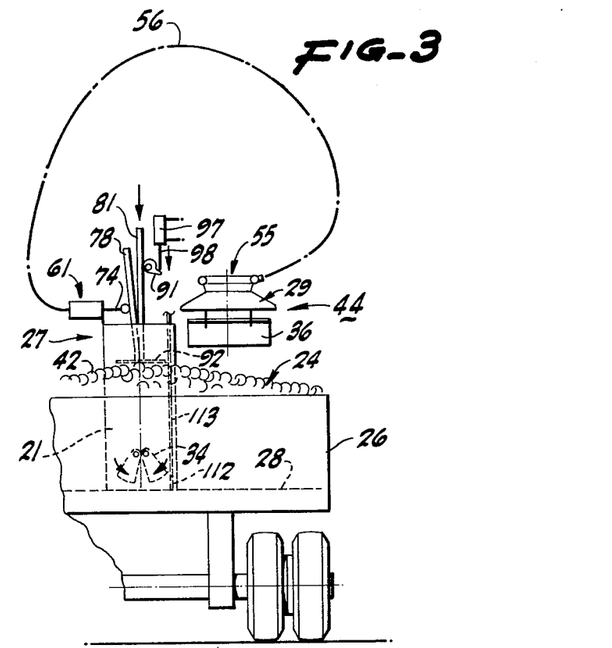
FIG. 3 is a view comparable to FIG. 2, but with the sampling tube in lower position, with the lower end jaws closing to confine the columnar sample within the sampling tube, and with the depth gauge in gauging position on the load.

Concurrently, the ram 98 has released the brake 91, allowing the depth gauge stem 81 freely to descend by gravity until the probe plate 92 abuts the top of the load, as in FIG. 3. The extent of downward movement of the depth gauge probe plate 92 is reflected in the extent of lateral displacement of the plunger 74, as operated on by the inclined cam plate 78. The plunger displacement, in turn, governs the amount of fluid driven through the connecting hose 56 to the toroid 55 and thus establishes a predetermined fluid pressure in the toroid.

The shallower the load 24, the greater the downward travel of the depth gauge and the larger the diameter 57 of the toroid. The higher the load, the smaller the diameter of the toroid.

When the jaws 34 have closed, the hoist 22 begins to lift the sampling tube 21. Simultaneously, the brake releasing jack 98 is retracted, allowing the bias spring 96 to rotate the eccentric 93 into locking position with respect to the depth probe stem 81, thereby temporarily immobilizing stem 81 as the sampling tube ascends. This braking action on the stem 81 prevents the stem from descending, i.e. staying in position with the plate 92 continuing to be supported by the load while the sampling tube ascends. The brake also maintains the status quo of the cam mechanism 78 so that the diameter of the toroid 55 remains at the dimension established by the displacement of fluid from the fluid source 61 as the depth gauge descended.

In uppermost position of the sampling tube 21, the separator 29 and the sample receptacle 36 are swung in the direction of the arrow 141 in FIG. 7 into axial alignment below the sampling tube 21 in order to receive the sample.

At this juncture, the jaws 34 are opened, as in FIG. 4, allowing the sample 33 to descend onto the subjacent toroid 55 and the separator 29. Only the core 32 can pass through toroid 55 and reach the sample box 36. The unwanted portion of the sample 33 surrounding the core 32 is intercepted by the sloping roof of the separator 29 and is laterally deflected to rejoin the main body of the load.

The contents of the separator box accurately reflect all horizons of the load as a consequence of the automatic depth gauging. By appropriately sloping the cam plate 78, core diameter is automatically adjusted to fill the sample box with the proper weight of representative material, from top to bottom, regardless of the load depth.

After the sample is filled, the arm 136 and separator 29 are moved by the plunger 131 in the direction of the arrow 142, as shown in FIG. 7.

Figure 5:
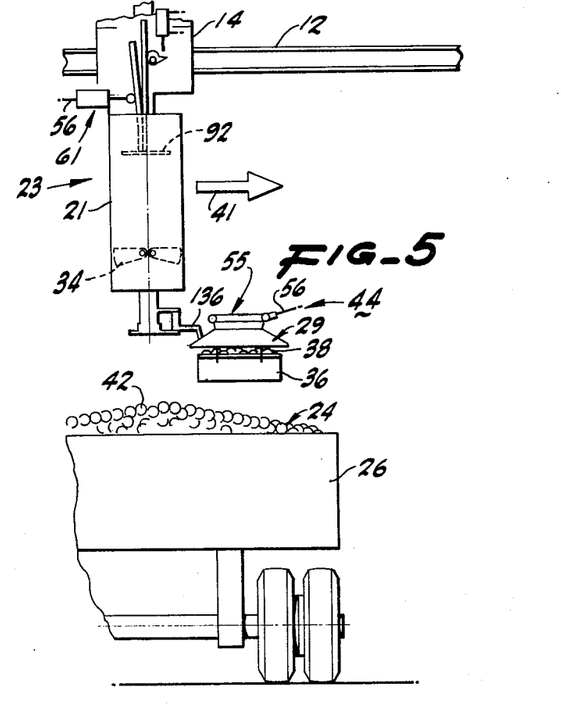
FIG. 5 is a view comparable to FIG. 2 but with the separator swung out from under the sampling tube and into alignment with the receptacle loading and unloading apparatus, preparatory to lateral movement of the trolley on the rail in order to deposit the receptacle adjacent the operator's platform shown in FIG. 1.

At this stage in the cycle, supported on wheels 144 supported on the rail 12 the trolley 14, is moved toward the right, in the direction of the arrow 41 in FIGS. 1 and 5, until the filled sample box 36 is deposited on the box lowering carriage 143 (see FIG. 1) and an empty replacement box is placed on the rails 37 depending from the separator 29.

The trolley direction is then reversed and the sampling apparatus is returned to central, or base, position awaiting the arrival of the next load and the resumption of the cycle.

It is to be noted that if the subsequent load is shallower than the first load, the brake releasing mechanism, including the ram 98, enables the probe plate 92 to descend even farther, until brought to a stop by supportive engagement with the top of the load, as before.

If, on the other hand, the subsequent load is greater in height than the first load, the probe plate 92 will be held in position on top of the load while the sampling tube 21 descends to the bottom of the load.

As previously indicated, the depth gauge 82 can be returned to uppermost, or base, position at any time, regardless of the condition of the brake mechanism 91 owing to the fact that the brake only limits downward movement of the gauge stem 81.

It can therefore be seen that a bulk load of fruits or vegetables, such as tomatoes, grapes, peaches, and the like, can be sampled with exemplary speed and accuracy by application of the variable opening concept to known structure.

What is claimed is:
1. A variable diameter toroidal device comprising:
   a. a resilient tube of predetermined length, inside diameter and outside diameter,
      said tube being curved in a circle with the ends located in close juxtaposition so that said tube forms a toroid of predetermined diameter;
   b. an uninterrupted helix of substantially non-resilient material embedded in said tube in coaxial relation, said helix being effective to resist forces exerted on said tube tending to change said predetermined inside and outside diameters of said tube and ineffective to resist forces exerted on said tube tending to change said predetermined length of said tube and said predetermined diameter of said toroid;
   c. means communicating with fluid inside said tube for selectively establishing the pressure of said fluid, said predetermined diameter of said toroid being dependent upon the forces exerted on said tube by said fluid pressure.

2. A device as in claim 1 in which said pressure establishing means includes a T-shaped pipe fitting with the cross limbs of said fitting inserted in said ends of said tube, and with the vertical limb projecting from said ends of said tube for communication with said fluid pressure establishing means.

3. A device as in claim 1 including a ring of fixed diameter disposed in a plane parallel to and spaced from the plane of said toroid; a plurality of arms pivotally mounted at one end of said ring and at the other end on said toroid, said arms maintaining said toroid in spaced coaxial relation and defining a throat having a selectively variable cross-sectional area in the vicinity of said toroid as said predetermined diameter of said toroid is varied in response to said pressure establishing means.

4. A device as in claim 3 further including a truncated cone-like separator having an upper circular margin substantially coincident with said fixed diameter ring; means for mounting said fixed diameter ring on said margin with said toroid vertically above said ring; and a receptacle below said separator to receive a desired portion of the material passing downwardly through said throat, the other undesired portion of the material being deflected away from said receptacle by the upper surfaces of said separator.

5. A device as in claim 4 further including a vertical hoist column; a vertically translatable sampling tube on said hoist column movable between a first upward position above a load of material to be sampled and a second downward position wherein the lower end of said sampling tube is adjacent the bottom of the load; means for closing off said lower end of said sampling tube in said second position so that when the sampling tube is thereafter moved toward said first position said sampling tube contains a columnar sample of said load from top to bottom; means for releasing said sample from said sampling tube in said first position; means mounting said separator on said column for moving separator between a first location axially below said lower end of said sampling tube when said sampling tube is in said first position and a second location removed from said sampling tube when said sampling tube is in other than said first position; means for lifting and lowering said sampling tube between said first position and said second position; and means for moving said separator between said first location and said second location.

6. A device as in claim 5 further including means connected to said fluid pressure establishing means for varying said fluid pressure in said toroid in dependence upon the extent of vertical penetration of said sampling tube into said load as said sampling tube is moved from said first position to said second position; and means for maintaining the established fluid pressure in said toroid as said sampling tube with contained sample is moved from said second position to said first position and said separator is moved to said first location.

7. An apparatus for sampling a crop from a load of given height, said apparatus comprising;
 a. a frame including a rail located above said load;
 b. a hoist column suspended from said rail;
 c. a sampling tube translatably mounted on said hoist column for vertical movement between an upper first position above said load and a second lower position wherein the lower end of said sampling tube is adjacent the bottom of said load;
 d. separator means on said frame for accepting only a predetermined portion of a load sample released from said sampling tube, said separator means being adjustable in dependence upon the height of said load and being movable between a first location axially below said sampling tube in said first position thereof and a second location removed from said sampling tube in any position thereof other than said first position;
 e. means for translating said sampling tube between said first end said second positions; and,
 f. means for moving said separator means between said first location and said second location.

8. An apparatus as in claim 7 in which said separator means includes an extensible fluid-filled tube formed into an enclosure defining a horizontal opening coaxial with said sampling tube in said first location of said separator, the area of said opening varying in dependence upon the fluid pressure within said tube; a receptacle below said opening to receive said predetermined portion of said load sample passing downwardly through said opening; means for deflecting the portion of said load sample other than said predetermined portion; and means for establishing said fluid pressure in dependence upon the height of said load.

9. An apparatus as in claim 8 in which said pressure establishing means includes a pressure source in communication with the fluid within said tube; and a valve interposed in the fluid pressure line between said pressure source and said tube.

10. An apparatus as in claim 8 in which said pressure establishing means includes a fluid displacement device and means in communication with said device and said tube for displacing fluid between said device and said tube in dependence upon the extent of travel of said sampling tube while penetrating said load.

11. An apparatus as in claim 10 in which said fluid displacement device includes a plunger and cylinder; said fluid displacing means includes a load depth gauge carried on said sampling tube; and cam means on said depth gauge in engagement with said plunger for displacing fluid from said device into said tube as said depth gauge measures the height of said load.

12. An apparatus as in claim 11 in which said depth gauge includes a vertically translatable stem; and a stop plate mounted on the lower end of said stem engageable with the top of said load, said cam means being movable with said stem.

* * * * *